United States Patent [19]

Dryja et al.

[11] Patent Number: 5,225,546
[45] Date of Patent: Jul. 6, 1993

[54] DIAGNOSIS OF HEREDITARY RETINAL DEGENERATIVE DISEASE

[75] Inventors: Thaddeus P. Dryja, Milton; Eliot L. Berson, Boston, both of Mass.

[73] Assignee: President and Fellows of Harvard College, Cambridge, Mass.

[21] Appl. No.: 825,296

[22] Filed: Jan. 23, 1992

Related U.S. Application Data

[63] Continuation of Ser. No. 469,215, Jan. 24, 1990, abandoned.

[51] Int. Cl.$^5$ .......................... C07H 21/04; C12Q 1/68
[52] U.S. Cl. ............................... 536/24.31; 435/6; 536/24.3; 935/77; 935/78
[58] Field of Search ................. 435/6; 536/26, 27, 28, 536/29

[56] References Cited

U.S. PATENT DOCUMENTS 4,683,195 7/1987 Mullis et al. ............................ 435/6
4,736,866 4/1988 Leder et al. ............................ 435/6

OTHER PUBLICATIONS

Tuteja et al., FEBS Lett. 232G): 182–186 (May 1988).
McWilliams et al., Genomics 5:619–622, 1989.
Sparkes et al., Invest. Ophthalmol. Vis. Sci. 27:1170–1172, 1986.
Weber and May, Am. J. Hum. Genet. 44:388–396, 1989.
Nathans et al., Science 232:203–210, 1986.
Applebury and Hargrave, Vision Res. 26:1881–1895, 1986.
Sparkes et al., Current Eye Research 5:797–798, 1986.
Berson et al., Arch. Ophthal. 80:58–67, 1968.
Reichel et al., Am. J. Ophthal. 108:540–547, 1989.
Nathans et al., Proceedings of National Academy of Science (USA), vol. 81, 1984, pp. 4851–4855.
Nathans et al., Science, vol. 232, 1986, pp. 193–202.
Medyniski et al., Proceedings of the National Academy of Sciences (USA), vol. 82, 1985, pp. 4311–4315.

*Primary Examiner*—Margaret Moskowitz
*Assistant Examiner*—Stephanie W. Zitomer
*Attorney, Agent, or Firm*—Fish & Richardson

[57] ABSTRACT

A probe/primer which includes a substantially purified single stranded oligonucleotide containing a region the sequence of which is identical to the sequence of a six-nucleotide, single-stranded segment of a gene encoding a mutant form of a human photoreceptor protein, which segment includes the mutation; and methods of making and using such probe/primer.

6 Claims, 18 Drawing Sheets

```
                                    GTATGAGCCG... Intron 1 ...TGCCTTGCAG
609                 624                      639                   654
TTC GGG CCC ACA GGA TGC AAT TTG GAG GGC TTC TTT GCC ACC CTG GGC GGT
Phe Gly Pro Thr Gly Cys Asn Leu Glu Gly Phe Phe Ala Thr Leu Gly Gly
                                                                120

2452                    2467                   2482
GAA ATT GCC CTG TGG TCC TTG GTG GTC CTG GCC ATC GAG CGG TAC GTG GTG
Glu Ile Ala Leu Trp Ser Leu Val Val Leu Ala Ile Glu Arg Tyr Val Val 2497                    2512                     2527              2542
GTG TGT AAG CCC ATG AGC AAC TTC CGC TTC GGG GAG AAC CAT GCC ATC ATG
Val Cys Lys Pro Met Ser Asn Phe Arg Phe Gly Glu Asn His Ala Ile Met
        140

2557                    2572                    2587
GGC GTT GCC TTC ACC TGG GTC ATG GCG CTG GCC TGC GCC GCA CCC CCA CTC
Gly Val Ala Phe Thr Trp Val Met Ala Leu Ala Cys Ala Ala Pro Pro Leu
                160

GTAATGGCAC... Intron 2 ...CTGTCCTCAG 2602                         3828                   3843
GCC GGC TGG TCC AGG TAC ATC CCC GAG GGC CTG CAG TGC TCG TGT GGA ATC
Ala Gly Trp Ser Arg Tyr Ile Pro Glu Gly Leu Gln Cys Ser Cys Gly Ile
                            180

3858                    3873                   3888
GAC TAC TAC ACG CTC AAG CCG GAG GTC AAC AAC GAG TCT TTT GTC ATC TAC
Asp Tyr Tyr Thr Leu Lys Pro Glu Val Asn Asn Glu Ser Phe Val Ile Tyr
                                            200

3903                3918                    3933                   3948
ATG TTC GTG GTC CAC TTC ACC ATC CCC ATG ATT ATC ATC TTT TTC TGC TAT
Met Phe Val Val His Phe Thr Ile Pro Met Ile Ile Ile Phe Phe Cys Tyr
                                                                220

GTACGGGCCG... Intron 3 ...TGTCCTGCAG 3963                3978           4109
GGG CAG CTC GTC TTC ACC GTC AAG GAG GCC GCT GCC CAG CAG CAG GAG TCA
Gly Gln Leu Val Phe Thr Val Lys Glu Ala Ala Ala Gln Gln Gln Glu Ser
                                                                240
```

FIG. 1b

```
       4124                    4139                        4154                      4169
GCC ACC ACA CAG AAG GCA GAG AAG GAG GTC ACC CGG ATG GTC ATC ATC ATG
Ala Thr Thr Gln Lys Ala Glu Lys Glu Val Thr Arg Met Val Ile Ile Met 4184                    4199                    4214
GTC ATC GCT TTC CTG ATC TGC TGG GTG CCC TAC GCC AGC GTG GCA TTC TAC
Val Ile Ala Phe Leu Ile Cys Trp Val Pro Tyr Ala Ser Val Ala Phe Tyr
            260

4229                    4244                    4259
ATC TTC ACC CAC CAG GGC TCC AAC TTC GGT CCC ATC TTC ATG ACC ATC CCA
Ile Phe Thr His Gln Gly Ser Asn Phe Gly Pro Ile Phe Met Thr Ile Pro
                        280

4274                 4289                    4304                    4319
GCG TTC TTT GCC AAG AGC GCC GCC ATC TAC AAC CCT GTC ATC TAT ATC ATG
Ala Phe Phe Ala Lys Ser Ala Ala Ile Tyr Asn Pro Val Ile Tyr Ile Met
                                    300

GTGCCTACTG... Intron 4 ...TGCCTTCCAG 4334                 5182                    5197
ATG AAC AAG CAG TTC CGG AAC TGC ATG CTC ACC ACC ATC TGC TGC CGC AAG
Met Asn Lys Gln Phe Arg Asn Cys Met Leu Thr Thr Ile Cys Cys Arg Lys
                                            320

5212                    5227                 5242               5257
AAC CCA CTG GGT GAC GAT CAG GCC TCT GCT ACC GTG TCC AAG ACG GAG ACG
Asn Pro Leu Gly Asp Asp Gln Ala Ser Ala Thr Val Ser Lys Thr Glu Thr
                                                            340

5272              5285         5295          5305
AGC CAG GTG GCC CCG GCC TAAGACCTGC CTAGGACTCT GTGGCCGACT
Ser Gln Val Ala Pro Ala
                348

5315       5325       5335       5345       5355       5365
      ATAGGCGTCT CCCATCCCCT ACACCTTCCC CCAGCCACAG CCATCCCACC AGGAGCAGCG 5375       5385       5395       5405       5415       5425
      CCTGTGCAGA ATGAACGAAG TCACATAGGC TCCTTAATTT TTTTTTTTTT TTTAAGAAAT 5435       5445       5455       5465       5475       5485
      AATTAATGAG GCTCCTCACT CACCTGGGAC AGCCTGAGAA GGGACATCCA CCAAGACCTA 5495       5505       5515       5525       5535       5545
      CTGATCTGGA GTCCCACGTT CCCCAAGGCC AGCGGGATGT GTGCCCCTCC TCCTCCCAAC
```

FIG. 1c

```
         5555       5565       5575       5585       5595       5605
   TCATCTTTCA GGAACACGAG GATTCTTGCT TTCTGGAAAA GTGTCCCAGC TTAGGGATAA 5615       5625       5635       5645       5655       5665
   GTGTCTAGCA CAGAATGGGG CACACAGTAG GTGCTTAATA AATGCTGGAT GGATGCAGGA 5675       5685       5695       5705       5715       5725
   AGGAATGGAG GAATGAATGG GAAGGGAGAA CATATCTATC CTCTCAGACC CTCGCAGCAG 5735       5745       5755       5765       5775       5785
   CAGCAACTCA TACTTGGCTA ATGATATGGA GCAGTTGTTT TTCCCTCCCT GGGCCTCACT 5795       5805       5815       5825       5835       5845
   TTCTTCTCCT ATAAAATGGA AATCCAGAT  CCCTGGTCCT GCCGACACGC AGCTACTGAG 5855       5865       5875       5885       5895       5905
   AAGACCAAAA GAGGTGTGTG TGTGTCTATG TGTGTGTTTC AGCACTTTGT AAATAGCAAG 5915       5925       5935       5945       5955       5965
   AAGCTGTACA GATTCTAGTT AATGTTGTGA ATAACATCAA TTAATGTAAC TAGTTAATTA 5975       5985       5995       6005       6015       6025
   CTATGATTAT CACCTCCTGA TAGTGAACAT TTTGAGATTG GGCATTCAGA TGATGGGGTT 6035       6045       6055       6065       6075       6085
   TCACCCAACC TTGGGGCAGG TTTTTAAAAA TTAGCTAGGC ATCAAGGCCA GACCAGGGCT 6095       6105       6115       6125       6135       6145
   GGGGGTTGGG CTGTAGGCAG GGACAGTCAC AGGAATGCAG GATGCAGTCA TCAGACCTGA 6155       6165       6175       6185       6195       6205
   AAAAACAACA CTGGGGGAGG GGGACGGTGA AGGCCAAGTT CCCAATGAGG GTGAGATTGG 6215       6225       6235       6245       6255       6265
   GCCTGGGGTC TCACCCCTAG TGTGGGGCCC CAGGTCCCGT GCCTCCCCTT CCCAATGTGG 6275       6285       6295       6305       6315       6325
   CCTATGGAGA GACAGGCCTT TCTCTCAGCC TCTGGAAGCC ACCTGCTCTT TTGCTCTAGC 6335       6345       6355       6365       6375       6385
   ACCTGGGTCC CAGCATCTAG AGCATGGAGC CTCTAGAAGC CATGCTCACC CGCCCACATT 6395       6405       6415       6425       6435       6445
   TAATTAACAG CTGAGTCCCT GATGTCATCC TTACTCGAAG AGCTTAGAAA CAAAGAGTGG 6455       6465       6475       6485       6495       6505
   GAAATTCCAC TGGGCCTACC TTCCTTGGGG ATGTTCATGG GCCCCAGTTT CCAGTTTCCC 6515       6525       6535       6545       6555       6565
   TTGCCAGACA AGCCCATCTT CAGCAGTTGC TAGTCCATTC TCCATTCTGG AGAATCTGCT
```

FIG. 1d

```
           6575       6585       6595       6605       6615       6625
     CCAAAAAGCT GGCCACATCT CTGAGGTGTC AGAATTAAGC TGCCTCAGTA ACTGCTCCCC 6635       6645       6655       6665       6675       6685
     CTTCTCCATA TAAGCAAAGC CAGAAGCTCT AGCTTTACCC AGCTCTGCCT GGAGACTAAG 6695       6705       6715       6725       6735       6745
     GCAAATTGGG CCATTAAAAG CTCAGCTCCT ATGTTGGTAT TAACGGTGGT GGGTTTTGTT 6755       6765       6775       6785       6795       6805
     GCTTTCACAC TCTATCCACA GGATAGATTG AAACTGCCAG CTTCCACCTG ATCCCTGACC 6815       6825       6835       6845       6855       6865
     CTGGGATGGC TGGATTGAGC AATGAGCAGA GCCAAGCAGC ACAGAGTCCC CTGGGGCTAG 6875       6885       6895       6905       6915       6925
     AGGTGGAGGA CGCAGTCCTG GGAATGGGAA AAACCCCAAC TTTGGGGTCA TAGAGGCACA 6935       6945
     GGTAACCCAT AAAACTGCAA ACAAGCTT
```

FIG. 1e

```
GGATCCTGAG TACCTCTCCT CCCTGACCTC AGGCTTCCTC CTAGTGTCAC CTTGGCCCCT   60
CCTAGGACTC ATGGAGAGGA GGGACTGGAG TCCGAAGGAG GATCACAGTG GAACCGGGGA

CTTAGAAGCC AATTAGGCCC TCAGTTTCTG CAGCGGGGAT TAATATGATT ATGAACACCC  120
GAATCTTCGG TTAATCCGGG AGTCAAAGAC GTCGCCCCTA ATTATACTAA TACTTGTGGG

CCAATCTCCC AGATGCTGAT TCAGCCAGGA GCTTAGGAGG GGGAGGTCAC TTTATAAGGG  180
GGTTAGAGGG TCTACGACTA AGTCGGTCCT CGAATCCTCC CCCTCCAGTG AAATATTCCC

TCTGGGGGGG TCAGAACCCA GAGTCATCCA GCTGGAGCCC TGAGTGGCTG AGCTCAGGCC  240
AGACCCCCCC AGTCTTGGGT CTCAGTAGGT CGACCTCGGG ACTCACCGAC TCGAGTCCGG
   #348 →

TTCGCAGCAT TCTTGGGTGG GAGCAGCCAC GGGTCAGCCA CAAGGGCCAC AGCCATGAAT  300
AAGCGTCGTA AGAACCCACC CTCGTCGGTG CCCAGTCGGT GTTCCCGGTG TCGGTACTTA

GGCACAGAAG GCCCTAACTT CTACGTGCCC TTCTCCAATG CGACGGGTGT GGTACGCAGC  360
CCGTGTCTTC CGGGATTGAA GATGCACGGG AAGAGGTTAC GCTGCCCACA CCATGCGTCG

CCCTTCGAGT ACCCACAGTA CTACCTGGCT GAGCCATGGC AGTTCTCCAT GCTGGCCGCC  420
GGGAAGCTCA TGGGTGTCAT GATGGACCGA CTCGGTACCG TCAAGAGGTA CGACCGGCGG

TACATGTTTC TGCTGATCGT GCTGGGCTTC CCCATCAACT TCCTCACGCT CTACGTCACC  480
ATGTACAAAG ACGACTAGCA CGACCCGAAG GGGTAGTTGA AGGAGTGCGA GATGCAGTGG

GTCCAGCACA AGAAGCTGCG CACGCCTCTC AACTACATCC TGCTCAACCT AGCCGTGGCT  540
CAGGTCGTGT TCTTCGACGC GTGCGGAGAG TTGATGTAGG ACGAGTTGGA TCGGCACCGA

GACCTCTTCA TGGTCCTAGG TGGCTTCACC AGCACCCTCT ACACCTCTCT GCATGGATAC  600
CTGGAGAAGT ACCAGGATCC ACCGAAGTGG TCGTGGGAGA TGTGGAGAGA CGTACCTATG

TTCGTCTTCG GGCCCACAGG ATGCAATTTG GAGGGCTTCT TTGCCACCCT GGGCGGTATG  660
AAGCAGAAGC CCGGGTGTCC TACGTTAAAC CTCCCGAAGA AACGGTGGGA CCCGCCATAC

AGCCGGGTGT GGGTGGGGTG TGCAGGAGCC CGGGAGCATG GAGGGGTCTG GAGAGTCCC   720
TCGGCCCACA CCCACCCCAC ACGTCCTCGG GCCCTCGTAC CTCCCCAGAC CCTCTCAGGG

GGGCTTGGCG GTGGTGGCTG AGAGGCCTTC TCCCTTCTCC TGTCCTGTCA ATGTTATCCA  880
CCCGAACCGC CACCACCGAC TCTCCGGAAG AGGGAAGAGG ACAGGACAGT TACAATAGGT
                                                   ← #349

AAGCCCTCAT ATATTCAGTC AACAAACACC ATTCATGGTG ATAGCCGGGC TGCTGTTTGT  840
TTCGGGAGTA TATAAGTCAG TTGTTTGTGG TAAGTACCAC TATCGGCCCG ACGACAAACA

GCAGGGCTGG CACTGAACAC TGCCTTGATC TTATTTGGAG CAATATGCGC TTGTCTAATT  900
CGTCCCGACC GTGACTTGTG ACGGAACTAG AATAAACCTC GTTATACGCG AACAGATTAA

TCACAGCAAG AAAACTGAGC TGAGGCTCAA AGGCCAAGTC AAGCCCCTGC TGGGGCGTCA  960
AGTGTCGTTC TTTTGACTCG ACTCCGAGTT TCCGGTTCAG TTCGGGGACG ACCCCGCAGT

CACAGGGACG GGTGCAGAGT TGAGTTGGAA GCCCGCATCT ATCTCGGGCC ATGTTTGCAG 1020
GTGTCCCTGC CCACGTCTCA ACTCAACCTT CGGGCGTAGA TAGAGCCCGG TACAAACGTC
```

FIG. 2a

```
CACCAAGCCT CTGTTTCCCT TGGAGCAGCT GTGCTGAGTC AGACCCAGGC TGGGCACTGA 1080
GTGGTTCGGA GACAAAGGGA ACCTCGTCGA CACGACTCAG TCTGGGTCCG ACCCGTGACT

GGGAGAGCTG GGCAAGCCAG ACCCCTCCTC TCTGGGGGCC CAAGCTCAGG GTGGGAAGTG 1140
CCCTCTCGAC CCGTTCGGTC TGGGGAGGAG AGACCCCCGG GTTCGAGTCC CACCCTTCAC

GATTTTCCAT TCTCCAGTCA TTGGGTCTTC CCTGTGCTGG GCAATGGGCT CGGTCCCCTC 1200
CTAAAAGGTA AGAGGTCAGT AACCCAGAAG GGACACGACC CGTTACCCGA GCCAGGGGAG

TGGCATCCTC TGCCTCCCCT CTCAGCCCCT GTCCTCAGGT GCCCCTCCAG CCTCCCTGCC 1260
ACCGTAGGAG ACGGAGGGGA GAGTCGGGGA CAGGAGTCCA CGGGGAGGTC GGAGGGACGG

GCGTTCCAAG TCTCCTGGTG TTGAGAACCG CAAGCAGCCG CTCTGAAGCA GTTCCTTTTT 1320
CGCAAGGTTC AGAGGACCAC AACTCTTGGC GTTCGTCGGC GAGACTTCGT CAAGGAAAAA

GCTTTAGAAT AATGTCTTGC ATTTAACAGG AAAACAGATG GGGTGCTGCA GGGATAACAG 1380
CGAAATCTTA TTACAGAACG TAAATTGTCC TTTTGTCTAC CCCACGACGT CCCTATTGTC

ATCCCACTTA ACAGAGAGGA AAACTGAGGC AGGGAGAGGG GAAGAGACTC ATTTAGGGAT 1400
TAGGGTGAAT TGTCTCTCCT TTTGACTCCG TCCCTCTCCC CTTCTCTGAG TAAATCCCTA

GTGGCCAGGC AGCAACAAGA GCCTAGGTCT CCTGGCTGTG ATCCAGGAAT ATCTCTGCTG 1500
CACCGGTCCG TCGTTGTTCT CGGATCCAGA GGACCGACAC TAGGTCCTTA TAGAGACGAC

AGATGCAGGA GGAGACGCTA GAAGCAGCCA TTGCAAAGCT GGGTGACGGG GAGAGCTTAC 1560
TCTACGTCCT CCTCTGCGAT CTTCGTCGGT AACGTTTCGA CCCACTGCCC CTCTCGAATG

CGCCAGCCAC AAGCGTCTCT CTGCCAGCCT TGCCCTGTCT CCCCCATGTC CAGGCTGCTG 1620
GCGGTCGGTG TTCGCAGAGA GACGGTCGGA ACGGGACAGA GGGGGTACAG GTCCGACGAC

CCTCGGTCCC ATTCTCAGGG AATCTCTGGC CATTGTTGGG TGTTTGTTGC ATTCAATAAT 1680
GGAGCCAGGG TAAGAGTCCC TTAGAGACCG GTAACAACCC ACAAACAACG TAAGTTATTA

CACAGATCAC TCAGTTCTGG CCAGAAGGTG GGTGTGCCAC TTACGGGTGG TTGTTCTCTG 1740
GTGTCTAGTG AGTCAAGACC GGTCTTCCAC CCACACGGTG AATGCCCACC AACAAGAGAC

CAGGGTCAGT CCCAGTTTAC AAATATTGTC CCTTTCACTG TTAGGAATGT CCCAGTTTGG 1800
GTCCCAGTCA GGGTCAAATG TTTATAACAG GGAAAGTGAC AATCCTTACA GGGTCAAACC

TTGATTAACT ATATGGCCAC TCTCCCTATG AAACTTCATG GGGTGGTGAG CAGGACAGAT 1860
AACTAATTGA TATACCGGTG AGAGGGATAC TTTGAAGTAC CCCACCACTC GTCCTGTCTA
                                   #364 ──────▶
GTTCGAATTC CATCATTTCC TTCTTCTTCC TCTGGGCAAA ACATTGCACA TTGCTTCATG 1920
CAAGCTTAAG GTAGTAAAGG AAGAAGAAGG AGACCCGTTT TGTAACGTGT AACGAAGTAC

GCTCCTAGGA GAGGCCCCCA CATGTCCGGG TTATTTCATT TCCCGAGAAG GGAGAGGGAG 1980
CGAGGATCCT CTCCGGGGGT GTACAGGCCC AATAAAGTAA AGGGCTCTTC CCTCTCCCTC

GAAGGACTGC CAATTCTGGG TTTCCACCAC CTCTGCATTC CTTCCCAACA AGGAACTCTG 2040
CTTCCTGACG GTTAAGACCC AAAGGTGGTG GAGACGTAAG GAAGGGTTGT TCCTTGAGAC

CCCCACATTA GGATGCATTC TTCTGCTAAA CACACACACA CACACACACA CACACAACAC 2100
GGGGTGTAAT CCTACGTAAG AAGACGATTT GTGTGTGTGT GTGTGTGTGT GTGTGTTGTG

ACACACACAC ACACACACAC ACACACACAC AAAACTCCCT ACCGGGTTCC CAGTTCAATC 2160
TGTGTGTGTG TGTGTGTGTG TGTGTGTGTG TTTTGAGGGA TGGCCCAAGG GTCAAGTTAG
```

FIG. 2b

```
CTGACCCCCT GATCTGATTC GTGTCCCTTA TGGGCCCAGA GCGCTAAGCA AATAACTTCC 2220
GACTGGGGGA CTAGACTAAG CACAGGGAAT ACCCGGGTCT CGCGATTCGT TTATTGAAGG
                                           ←─────  #365
CCCATTCCCT GGAATTTCTT TGCCCAGCTC TCCTCAGCGT GTGGTCCCTC TGCCCCTTCC 2280
GGGTAAGGGA CCTTAAAGAA ACGGGTCGAG AGGAGTCGCA CACCAGGGAG ACGGGGAAGG

CCCTCCTCCC AGCACCAAGC TCTCTCCTTC CCAAGGCCT CCTCAAATCC CTCTCCCACT 2340
GGGAGGAGGG TCGTGGTTCG AGAGAGGAAG GGGTTCCGGA GGAGTTTAGG GAGAGGGTGA
                                     #346 ─────▶
CCTGGTTGCC TTCCTAGCTA CCCTCTCCCT GTCTAGGGGG GAGTGCACCC TCCTTAGGCA 2400
GGACCAACGG AAGGATCGAT GGGAGAGGGA CAGATCCCCC CTCACGTGGG AGGAATCCGT

GTGGGGTCTG TGCTGACCGC CTGCTGACTG CCTTGCAGGT GAAATTGCCC TGTGGTCCTT 2460
CACCCCAGAC ACGACTGGCG GACGACTGAC GGAACGTCCA CTTTAACGGG ACACCAGGAA

GGTGGTCCTG GCCATCGAGC GGTACGTGGT GGTGTGTAAG CCCATGAGCA ACTTCCGCTT 2520
CCACCAGGAC CGGTAGCTCG CCATGCACCA CCACACATTC GGGTACTCGT TGAAGGCGAA

CGGGGAGAAC CATGCCATCA TGGGCGTTGC CTTCACCTGG GTCATGGCGC TGGCCTGCGC 2580
GCCCCTCTTG GTACGGTAGT ACCCGCAACG GAAGTGGACC CAGTACGCGC ACCGGACGCG

CGCACCCCCA CTCGCCGGCT GGTCCAGGTA ATGGCACTGA GCAGAAGGGA AGAAGCTCCG 2640
GCGTGGGGGA GAGCGGCCGA CCAGGTCCAT TACCGTGACT CGTCTTCCCT TCTTCGAGGC

GGGGCTCTTT GTAGGGTCCT CCAGTCAGGA CTCAAACCCA GTAGTGTCTG GTTCCAGGCA 2700
CCCCGAGAAA CATCCCAGGA GGTCAGTCCT GAGTTTGGGT CATCACAGAC CAAGGTCCGT
          ─────  #347
CTGACCTTGT ATGTCTCCTG GCCCAAATGC CCACTCAGGG TAGGGGTGTA GGGCAGAAGA 2760
GACTGGAACA TACAGAGGAC CGGGTTTACG GGTGAGTCCC ATCCCCACAT CCCGTCTTCT

AGAAACAGAC TCTAATGTTG CTACAAGGGC TGGTCCCATC TCCTGAGCCC CATGTCAAAC 2820
TCTTTGTCTG AGATTACAAC GATGTTCCCG ACCAGGGTAG AGGACTCGGG GTACAGTTTG

AGAATCCAAG ACATCCCAAC CCTTCACCTT GGCTGTGCCC CTAATCCTCA ACTAAGCTAG 2880
TCTTAGGTTC TGTAGGGTTG GGAAGTGGAA CCGACACGGG GATTAGGAGT TGATTCGATC

GCGCAAATTC CAATCCTCTT TGGTCTAGTA CCCCGGGGGC AGCCCCTCT AACCTTGGGC 2940
CGCGTTTAAG GTTAGGAGAA ACCAGATCAT GGGGCCCCG TCGGGGAGA TTGGAACCCG

CTCAGCAGCA GGGGAGGCCA CACCTTCCTA GTGCAGGTGG CCATATTGTG GCCCCTTGGA 3000
GAGTCGTCGT CCCCTCCGGT GTGGAAGGAT CACGTCCACC GGTATAACAC CGGGGAACCT

ACTGGGTCCC ACTCAGCCTC TAGGCGATTG TCTCCTAATG GGGCTGAGAT GAGACTCAGT 3060
TGACCCAGGG TGAGTCGGAG ATCCGCTAAC AGAGGATTAC CCCGACTCTA CTCTGAGTCA

GGGGACAGTG GTTTGGACAA TAGGACTGGT GACTCTGGTC CCCAGAGGCC TCATGTCCCT 3120
CCCCTGTCAC CAAACCTGTT ATCCTGACCA CTGAGACCAG GGGTCTCCGG AGTACAGGGA

CTGTCTCCAG AAAATTCCCA CTCTCACTTC CCTTTCCTCC TCAGTCTTGC TAGGGTCCAT 3180
GACAGAGGTC TTTTAAGGGT GAGAGTGAAG GGAAAGGAGG AGTCAGAACG ATCCCAGGTA

TTCTACCCCT TGCTGAATTT GAGCCCACCC CCTGGACTTT TTCCCCATCT TCTCCAATCT 3240
AAGATGGGGA ACGACTTAAA CTCGGGTGGG GGACCTGAAA AAGGGGTAGA AGAGGTTAGA
```

FIG. 2c

```
GGCCTAGTTC TATCCTCTGG AAGCAGAGCC GCTGGACGCT CTGGGTTTCC TGAGGCCCGT 3300
CCGGATCAAG ATAGGAGACC TTCGTCTCGG CGACCTGCGA GACCCAAAGG ACTCCGGGCA

CCACTGTCAC CAATATCAGG AACCATTGCC ACGTCCTAAT GACGTGCGCT GGAAGCCTCT 3360
GGTGACAGTG GTTATAGTCC TTGGTAACGG TGCAGGATTA CTGCACGCGA CCTTCGGAGA

AGTTTCCAGA AGCTGCACAA AGATCCCTTA GATACTCTGT GTGTCCATCT TTGGCCTGGA 3420
TCAAAGGTCT TCGACGTGTT TCTAGGGAAT CTATGAGACA CACAGGTAGA AACCGGACCT

AAATACTCTC ACCCTGGGGC TAGGAAGACC TCGGTTTGTA CAAACTTCCT CAAATGCAGA 3480
TTTATGAGAG TGGGACCCCG ATCCTTCTGG AGCCAAACAT GTTTGAAGGA GTTTACGTCT

GCCTGAGGGC TCTCCCCACC TCCTCACCAA CCCTCTGCGT GGCATAGCCC TAGCCTCAGC 3540
CGGACTCCCG AGAGGGGTGG AGGAGTGGTT GGGAGACGCA CCGTATCGGG ATCGGAGTCG

GGGCAGTGGA TGCTGGGGCT GGGCATGCAG GGAGAGGCTG GGTGGTGTCA TCTGGTAACG 3600
CCCGTCACCT ACGACCCCGA CCCGTACGTC CCTCTCCGAC CCACCACAGT AGACCATTGC

CAGCCACCAA ACAATGAAGC GACACTGATT CCACAAGGTG CATCTGCATC CCCATCTGAT 3660
GTCGGTGGTT TGTTACTTCG CTGTGACTAA GGTGTTCCAC GTAGACGTAG GGGTAGACTA

CCATTCCATC CTGTCACCCA GCCATGCAGA CGTTTATGAT CCCCTTTTCC AGGGAGGGAA 3720
GGTAAGGTAG GACAGTGGGT CGGTACGTCT GCAAATACTA GGGGAAAAGG TCCCTCCCTT
                                                  #344
TGTGAAGCCC CAGAAAGGGC CAGCGCTCGG CAGCCACCTT GGCTGTTCCC AAGTCCCTCA 3780
ACACTTCGGG GTCTTTCCCG GTCGCGAGCC GTCGGTGGAA CCGACAAGGG TTCAGGGAGT

CAGGCAGGGT CTCCCTACCT GCCTGTCCTC AGGTACATCC CCGAGGGCCT GCAGTGCTCG 3840
GTCCGTCCCA GAGGGATGGA CGGACAGGAG TCCATGTAGG GGCTCCCGGA CGTCACGAGC

TGTGGAATCG ACTACTACAC GCTCAAGCCG GAGGTCAACA ACGAGTCTTT TGTCATCTAC 3900
ACACCTTAGC TGATGATGTG CGAGTTCGGC CTCCAGTTGT TGCTCAGAAA ACAGTAGATG

ATGTTCGTGG TCCACTTCAC CATCCCCATG ATTATCATCT TTTTCTGCTA TGGGCAGCTC 3960
TACAAGCACC AGGTGAAGTG GTAGGGGTAC TAATAGTAGA AAAAGACGAT ACCCGTCGAG

GTCTTCACCG TCAAGGAGGT ACGGGCCGGG GGGTGGGCGG CCTCACGGCT CTGAGGGTCC 4020
CAGAAGTGGC AGTTCCTCCA TGCCCGGCCC CCCACCCGCC GGAGTGCCGA GACTCCCAGG

AGCCCCAGC ATGCATCTGC GGCTCCTGCT CCCTGGAGGA GCCATGGTCT GGACCCGGGT 4080
TCGGGGTCG TACGTAGACG CCGAGGACGA GGGACCTCCT CGGTACCAGA CCTGGGCCCA

CCCGTGTCCT GCAGGCCGCT GCCCAGCAGC AGGAGTCAGC CACCACACAG AAGGCAGAGA 4140
GGGCACAGGA CGTCCGGCGA CGGGTCGTCG TCCTCAGTCG GTGGTGTGTC TTCCGTCTCT

AGGAGGTCAC CCGCATGGTC ATCATCATGG TCATCGCTTT CCTGATCTGC TGGGTGCCCT 4200
TCCTCCAGTG GGCGTACCAG TAGTAGTACC AGTAGCGAAA GGACTAGACG ACCCACGGGA

ACGCCAGCGT GGCATTCTAC ATCTTCACCC ACCAGGGCTC CAACTTCGGT CCCATCTTCA 4260
TGCGGTCGCA CCGTAAGATG TAGAAGTGGG TGGTCCCGAG GTTGAAGCCA GGGTAGAAGT

TGACCATCCC AGCGTTCTTT GCCAAGAGCG CCGCCATCTA CAACCCTGTC ATCTATATCA 4320
ACTGGTAGGG TCGCAAGAAA CGGTTCTCGC GGCGGTAGAT GTTGGGACAG TAGATATAGT
```

FIG. 2d

```
TGATGAACAA GCAGGTGCCT ACTGCGGGTG GGAGGGCCCC AGTGCCCCAG GCCACAGGCG 4380
ACTACTTGTT CGTCCACGGA TGACGCCCAC CCTCCCGGGG TCACGGGGTC CGGTGTCCGC

CTGCCTGCCA AGGACAAGCT ACTCCCAGGG CAGGGGAGGG GCTCCATCAG GGTTACTGGC 4440
GACGGACGGT TCCTGTTCGA TGAGGGTCCC GTCCCCTCCC CGAGGTAGTC CCAATGACCG
                       ← #345

AGCAGTCTTG GGTCAGCAGT CCCAATGGGG AGTGTGTGAG AAATGCAGAT TCCTGGCCCC 4500
TCGTCAGAAC CCAGTCGTCA GGGTTACCCC TCACACACTC TTTACGTCTA AGGACCGGGG

ACTCAGAACT GCTGAATCTC AGGGTGGGCC CAGGAACCTG CATTTCCAGC AAGCCCTCCA 4560
TGAGTCTTGA CGACTTAGAG TCCCACCCGG GTCCTTGGAC GTAAAGGTCG TTCGGGAGGT

CAGGTGGCTC AGATGCTCAC TCAGGTGGGA GAAGCTCCAG TCAGCTAGTT CTGGAAGCCC 4620
GTCCACCGAG TCTACGAGTG AGTCCACCCT CTTCGAGGTC AGTCGATCAA GACCTTCGGG

AATGTCAAAG TCAGAAGGAC CCAAGTCGGG AATGGGATGG GCCAGTCTCC ATAAAGCTGA 4660
TTACAGTTTC AGTCTTCCTG GGTTCAGCCC TTACCCTACC CGGTCAGAGG TATTTCGACT

ATAAGGAGCT AAAAAGTCTT ATTCTGAGGG GTAAAGGGGT AAAGGGTTCC TCGGAGAGGT 4740
TATTCCTCGA TTTTTCAGAA TAAGACTCCC CATTTCCCCA TTTCCCAAGG AGCCTCTCCA

ACCTCCGAGG GGTAAACAGT TGGGTAAACA GTCTCTGAAG TCAGCTCTGC CATTTTCTAG 4800
TGGAGGCTCC CCATTTGTCA ACCCATTTGT CAGAGACTTC AGTCGAGACG GTAAAAGATC

CTGTATGGCC CTGGGCAAGT CAATTTCCTT CTCTGTGCTT TGGTTTCCTC ATCCATAGAA 4860
GACATACCGG GACCCGTTCA GTTAAAGGAA GAGACACGAA ACCAAAGGAG TAGGTATCTT

AGGTAGAAAG GGCAAAACAC CAAACTCTTG GATTACAAGA GATAATTTAC AGAACACCCT 4920
TCCATCTTTC CCGTTTTGTG GTTTGAGAAC CTAATGTTCT CTATTAAATG TCTTGTGGGA

TGGCACACAG AGGGCACCAT GAAATGTCAC GGGTGACACA GCCCCCTTGT GCTCAGTCCC 4980
ACCGTGTGTC TCCCGTGGTA CTTTACAGTG CCCACTGTGT CGGGGGAACA CGAGTCAGGG

TGGCATCTCT AGGGGTGAGG AGCGTCTGCC TAGCAGGTTC CCACCAGGAA GCTGGATTTG 5040
ACCGTAGAGA TCCCCACTCC TCGCAGACGG ATCGTCCAAG GGTGGTCCTT CGACCTAAAC

AGTGGATGGG GCGCTGGAAT CGTGAGGGGC AGAAGCAGGC AAAGGGTCGG GGCGAACCTC 5100
TCACCTACCC CGCGACCTTA GCACTCCCCG TCTTCGTCCG TTTCCCAGCC CCGCTTGAG
            #350 →

ACTAACGTGC CAGTTCCAAG CACACTGTGG GCAGCCCTGG CCCTGACTCA AGCCTCTTGC 5160
TGATTGCACG GTCAAGGTTC GTGTGACACC CGTCGGGACC GGGACTGAGT TCGGAGAACG

CTTCCAGTTC CGGAACTGCA TGCTCACCAC CATCTGCTGC GGCAAGAACC CACTGGGTGA 5220
GAAGGTCAAG GCCTTGACGT ACGAGTGGTG GTAGACGACG CCGTTCTTGG GTGACCCACT

CGATGAGGCC TCTGCTACCG TGTCCAAGAC GGAGACGAGC CAGGTGGCCC CGGCCTAAGA 5280
GCTACTCCGG AGACGATGGC ACAGGTTCTG CCTCTGCTCG GTCCACCGGG GCCGGATTCT

CCTGCCTAGG ACTCTGTGGC CGACTATAGG CGTCTCCCAT CCCCTACACC TTCCCCCAGC 5340
GGACGGATCC TGAGACACCG GCTGATATCC GCAGAGGGTA GGGGATGTGG AAGGGGGTCG

CACAGCCATC CCACCAGGAG CAGCGCCTGT GCAGAATGAA CGAAGTCACA TAGGCTCCTT 5400
GTGTCGGTAG GGTGGTCCTC GTCGCGGACA CGTCTTACTT GCTTCAGTGT ATCCGAGGAA
                                 ← #351
```

FIG. 2e

```
AATTTTTTTT TTTTTTTTAA GAAATAATTA ATGAGGCTCC TCACTCACCT GGGACAGCCT 5460
TTAAAAAAAA AAAAAAAATT CTTTATTAAT TACTCCGAGG AGTGAGTGGA CCCTGTCGGA

GAGAAGGGAC ATCCACCAAG ACCTACTGAT CTGGAGTCCC ACGTTCCCCA AGGCCAGCGG 5520
CTCTTCCCTG TAGGTGGTTC TGGATGACTA GACCTCAGGG TGCAAGGGGT TCCGGTCGCC

GATGTGTGCC CCTCCTCCTC CCAACTCATC TTTCAGGAAC ACGAGGATTC TTGCTTTCTG 5580
CTACACACGG GGAGGAGGAG GGTTGAGTAG AAAGTCCTTG TGCTCCTAAG AACGAAAGAC

GAAAAGTGTC CCAGCTTAGG GATAAGTGTC TAGCACAGAA TGGGGCACAC AGTAGGTGCT 5640
CTTTTCACAG GGTCGAATCC CTATTCACAG ATCGTGTCTT ACCCCGTGTG TCATCCACGA

TAATAAATGC TGGATGGATG CAGGAAGGAA TGGAGGAATG AATGGGAAGG GAGAACATAT 5700
ATTATTTACG ACCTACCTAC GTCCTTCCTT ACCTCCTTAC TTACCCTTCC CTCTTGTATA

CTATCCTCTC AGACCCTCGC AGCAGCAGCA ACTCATACTT GGCTAATGAT ATGGAGCAGT 5760
GATAGGAGAG TCTGGGAGCG TCGTCGTCGT TGAGTATGAA CCGATTACTA TACCTCGTCA

TGTTTTTCCC TCCCTGGGCC TCACTTTCTT CTCCTATAAA ATGGAAATCC CAGATCCCTG 5820
ACAAAAAGGG AGGGACCCGG AGTGAAAGAA GAGGATATTT TACCTTTAGG GTCTAGGGAC

GTCCTGCCGA CACGCAGCTA CTGAGAAGAC CAAAAGAGGT GTGTGTGTGT CTATGTGTGT 5880
CAGGACGGCT GTGCGTCGAT GACTCTTCTG GTTTTCTCCA CACACACACA GATACACACA

GTTTCAGCAC TTTGTAAATA GCAAGAAGCT GTACAGATTC TAGTTAATGT TGTGAATAAC 5940
CAAAGTCGTG AAACATTTAT CGTTCTTCGA CATGTCTAAG ATCAATTACA ACACTTATTG

ATCAATTAAT GTAACTAGTT AATTACTATG ATTATCACCT CCTGATAGTG AACATTTGA  6000
TAGTTAATTA CATTGATCAA TTAATGATAC TAATAGTGGA GGACTATCAC TTGTAAAACT

GATTGGGCAT TCAGATGATG GGGTTTCACC CAACCTTGGG GCAGGTTTTT AAAAATTAGC 6060
CTAACCCGTA AGTCTACTAC CCCAAAGTGG GTTGGAACCC CGTCCAAAAA TTTTTAATCG

TAGGCATCAA GGCCAGACCA GGGCTGGGGG TTGGGCTGTA GGCAGGGACA GTCACAGGAA 6120
ATCCGTAGTT CCGGTCTGGT CCCGACCCCC AACCCGACAT CCGTCCCTGT CAGTGTCCTT

TGCAGGATGC AGTCATCAGA CCTGAAAAAA CAACACTGGG GGAGGGGAC GGTGAAGGCC 6180
ACGTCCTACG TCAGTAGTCT GGACTTTTTT GTTGTGACCC CCTCCCCCTG CCACTTCCGG

AAGTTCCCAA TGAGGGTGAG ATTGGGCCTG GGGTCTCACC CCTAGTGTGG GGCCCCAGGT 6240
TTCAAGGGTT ACTCCCACTC TAACCCGGAC CCCAGAGTGG GGATCACACC CCGGGGTCCA

CCCGTGCCTC CCCTTCCCAA TGTGGCCTAT GGAGAGACAG GCCTTTCTCT CAGCCTCTGG 6300
GGGCACGGAG GGGAAGGGTT ACACCGGATA CCTCTCTGTC CGGAAAGAGA GTCGGAGACC

AAGCCACCTG CTCTTTTGCT CTAGCACCTG GGTCCCAGCA TCTAGAGCAT GGAGCCTCTA 6360
TTCGGTGGAC GAGAAAACGA GATCGTGGAC CCAGGGTCGT AGATCTCGTA CCTCGGAGAT

GAAGCCATGC TCACCCGCCC ACATTTAATT AACAGCTGAG TCCCTGATGT CATCCTTACT 6420
CTTCGGTACG AGTGGGCGGG TGTAAATTAA TTGTCGACTC AGGGACTACA GTAGGAATGA

CGAAGAGCTT AGAAACAAAG AGTGGGAAAT TCCACTGGGC CTACCTTCCT TGGGGATGTT 6480
GCTTCTCGAA TCTTTGTTTC TCACCCTTTA AGGTGACCCG GATGGAAGGA ACCCCTACAA
```

FIG. 2f

```
CATGGGCCCC AGTTTCCAGT TTCCCTTGCC AGACAAGCCC ATCTTCAGCA GTTGCTAGTC 6540
GTACCCGGGG TCAAAGGTCA AAGGGAACGG TCTGTTCGGG TAGAAGTCGT CAACGATCAG

CATTCTCCAT TCTGGAGAAT CTGCTCCAAA AAGCTGGCCA CATCTCTGAG GTGTCAGAAT 6600
GTAAGAGGTA AGACCTCTTA GACGAGGTTT TTCGACCGGT GTAGAGACTC CACAGTCTTA

TAAGCTGCCT CAGTAACTGC TCCCCCTTCT CCATATAAGC AAAGCCAGAA GCTCTAGCTT 6660
ATTCGACGGA GTCATTGACG AGGGGGAAGA GGTATATTCG TTTCGGTCTT CGAGATCGAA

TACCCAGCTC TGCCTGGAGA CTAAGGCAAA TTGGGCCATT AAAAGCTCAG CTCCTATGTT 6720
ATGGGTCGAG ACGGACCTCT GATTCCGTTT AACCCGGTAA TTTTCGAGTC GAGGATACAA

GGTATTAACG GTGGTGGGTT TTGTTGCTTT CACACTCTAT CCACAGGATA GATTGAAACT 6780
CCATAATTGC CACCACCCAA ACAACGAAA GTGTGAGATA GGTGTCCTAT CTAACTTTGA

GCCAGCTTCC ACCTGATCCC TGACCCTGGG ATGGCTGGAT TGAGCAATGA GCAGAGCCAA 6840
CGGTCGAAGG TGGACTAGGG ACTGGGACCC TACCGACCTA ACTCGTTACT CGTCTCGGTT

GCAGCACAGA GTCCCCTGGG GCTAGAGGTG GAGGAGGCAG TCCTGGGAAT GGGAAAAACC 6900
CGTCGTGTCT CAGGGGACCC CGATCTCCAC CTCCTCCGTC AGGACCCTTA CCCTTTTTGG

CCAACTTTGG GGTCATAGAG GCACAGGTAA CCCATAAAAC TGCAAACAAG CTT         6960
GGTTGAAACC CCAGTATCTC CGTGTCCATT GGGTATTTTG ACGTTTGTTC GAA
```

FIG. 2g (a) 5' -     ACGCAGC<u>CA</u>CTTCGAGTAC    - 3'

(b) 5' -     ACGCAGC<u>CC</u>CTTCGAGTAC    - 3'

(c) 5' -       CGCAGC<u>CA</u>CTTCGAG     - 3'

(d) 5' -       CGCAGC<u>CC</u>CTTCGAG     - 3'

```
                 220                    240                    260
5' GCTGGAGCCC TGAGTGGCTG AGCTCAGGCC TTCGCAGCAT TCTTGGGTGG
3  GACCTCGGG  ACTCACCGAC TCGAGTCCGG AAGCGTCGTA AGAACCCACC 280                    300
   GAGCAGCCAC GGGTCAGCCA CAAGGGCCAC AGCCATGAAT
   CTCGTCGGTG CCCAGTCGGT GTTCCCGGTG TCGGTACTTA 320                             340
   GGCACAGAAG GCCCTAACTT CTACGTGCCC TTCTCCAATG CGACGGGTGT
   CCGTGTCTTC CGGGATTGAA GATGCACGGG AAGAGGTTAC GCTGCCCACA
              CODON
               28
             360                    380
   GGTACGCAGC CCCTTCGAGT ACCCACAGTA CTACCTGGCT          3'
   CCATGCGTCG GGGAAGCTCA TGGGTGTCAT GATGGACCGA          5'

TGAAGCTCA TGGGTGTCAT G        #502
                                            #485
```

FIG. 8

```
         10         20         30         40         50         60
CGGGGCTGTG CTGCACTTGA CCGCAGCAGG AGGGAGTCCA GGAGCCAAGG TTGCCGCGGT 70         80         90        100        110        120
GTCTCCGTCA GCCTCACCAT GAACCTGGAA CCGCCCAAGG CTGAGTTCCG GTCAGCCACC 130        140        150        160        170        180
AGGGTGGCCG GGGGACCTGT CACCCCCAGG AAAGGTCCCC CTAAATTTAA GCAGCGACAG 190        200        210        220        230        240
ACCAGGCAGT TCAAGAGCAA GCCCCCAAAG AAAGGCGTTC AAGGGTTTGG GGACGACATC 250        260        270        280        290        300
CCTGGAATGG AAGGCCTGGG AACAGACATC ACAGTCATCT GCCCTTGGGA GGCCTTCAAC 310        320        330        340        350        360
CACCTGGAGC TGCACGAGCT GGCCCAATAT GGCATCATCT AGCACGAGGC CCTGCTGAAG 370        380        390        400        410        420
TCCAGACCCT CCCCCTCCTG CCCACTGTGC TCTAAACCCT GCTCAGGATT CCTGTTGAGG 430        440        450        460        470        .480
AGATGCCTCC CTAGCCCAGA TGGCACCTGG ACACCAGGAT GGGACTGCAA CCTCAGGTCT 490        500        510        520        530        540
CCCCCTACAT ATTAATACCA GTCACCAGGA GCCCACCACC TCCCTCTAGG ATGCCCCCTC 550        560        570        580        590        600
AGGGGCTGGC CAGGCCCTGC TCAACATCTG GAGATACAGG CCCACCCCTC AGTCCTGCCC 610        620        630        640        650        660
ACAGAGAGGC TTGGTCGGTC TCCACTCCCA GGGAGAACGG GAAGTGGACC CCAGCCCGGG 670        680        690        700        710        720
AGCCTGCTGG ACCCCAGATC GTCCCCTCCT CCCAGCTGGA AAGCTAGGGC AGGTCTCCCC 730        740        750        760        770        780
AGAGTGCTTC TGCACCCCAG CCCCCTGTCC TGCCTGTAAG GGGATACAGA GAAGCTCCCC 790        800        810        820        830        840
GTCTCTGCAT CCCTTCCCAG GGGGGTGCCC TTAGTTTGGA CATGCTGGGT AGCAGGACTC 850        860        870        880        890        900
CAGGGCGTGC ACGGTGAGCA GATGAGGCCC CAAGCTCATC ACACCAGGGG GCCATCCTTC 910        920        930        940        950        960
TCAATACAGG CTGCCCTTGC AGTCCCTATT TCAAAATAAA ATTAGTGTGT CCTTGCCAAA

970
AAAAAAAAAA AAA
```

FIG. 10

```
ATG AAC CTG GAA CCG CCC AAG GCT GAG TTC CGG TCA GCC ACC AGG GTG GCC GGG GGA CCT
Met Asn Leu Glu Pro Pro Lys Ala Glu Phe Arg Ser Ala Thr Arg Val Ala Gly Gly Pro

GTC ACC CCC AGG AAA GGT CCC CCT AAA TTT AAG CAG CGA CAG ACC AGG CAG TTC AAG AGC
Val Thr Pro Arg Lys Gly Pro Pro Lys Phe Lys Gln Arg Gln Thr Arg Gln Phe Lys Ser

AAG CCC CCA AAG AAA GGC GTT CAA GGG TTT GGG GAC GAC ATC CCT GGA ATG GAA GGC CTG
Lys Pro Pro Lys Lys Gly Val Gln Gly Phe Gly Asp Asp Ile Pro Gly Met Glu Gly Leu

GGA ACA GAC ATC ACA GTC ATC TGC CCT TGG GAG GCC TTC AAC CAC CTG GAG CTG CAC GAG
Gly Thr Asp Ile Thr Val Ile Cys Pro Trp Glu Ala Phe Asn His Leu Glu Leu His Glu

CTG GCC CAA TAT GGC ATC ATC TAG
Leu Ala Gln Tyr Gly Ile Ile End
```

FIG. 11

DIAGNOSIS OF HEREDITARY RETINAL DEGENERATIVE DISEASE

This is a continuation of application Ser. No. 07/469,215, filed Jan. 24, 1990, now abandoned.

BACKGROUND OF THE INVENTION

The field of the invention is detection of genetic abnormalities in humans.

The hereditary retinal degenerative diseases ("HRD diseases") are a group of inherited conditions in which progressive, bilateral degeneration of retinal structures leads to loss of retinal function; these diseases include, for example, age-related macular degeneration, a leading cause of visual impairment in the elderly; Leber's congenital amaurosis, which causes its victims to be born blind; and retinitis pigmentosa ("RP"). RP is the name given to those inherited retinopathies which are characterized by loss of retinal photoreceptors (rods and cones), with retinal electrical responses to light flashes (i.e. electroretinograms, or "ERGs") that are reduced in amplitude. As the disease progresses, patients show attenuated retinal arterioles, and frequently show "bone spicule" pigmentation of the retina and waxy pallor of the optic discs.

The incidence of RP in the United States is estimated to be about 1:3500 births. Approximately 43% of cases in the state of Maine are from families with an autosomal dominant mode of transmission, 20% autosomal recessive, and 8% X-linked; 23% are isolated cases and 6% are undetermined (e.g., adopted) (Bunker et al., Am. J. Ophthalmol. 97:357–365, 1984). Genetic heterogeneity is thought to exist within each hereditary pattern. For example, linkage studies have revealed at least two distinct genetic loci for RP on the X-chromosome (Chen, Am. J. Hum. Genet. 45:401–411, 1989), another possibly near the rhesus locus on chromosome 1p (Yijian et al., Cytogenet. Cell Genet. 46:614, 1987), and a fourth on the long arm of chromosome 3 (McWilliam et al., Genomics 5:619–622, 1989). Hence, RP is not one disease, but a group of diseases caused by mutations at various loci within the human genome.

Familial cases of RP usually present in childhood with night blindness and loss of midperipheral visual field due to the loss of rods in the peripheral retina. As the condition progresses, contraction of the visual fields eventually leads to blindness. Signs on fundus examination in advanced stages include retinal vessel attenuation, intraretinal pigment in the peripheral fundus, and waxy pallor of the optic disc. Patients have abnormal light-evoked electrical responses from the retina (i.e., electroretinograms or ERGs), even in the early stages in the absence of visible abnormalties on fundus examination. Histopathologic studies have revealed widespread loss of photoreceptors in advanced stages.

SUMMARY OF THE INVENTION

In general, the invention features a probe/primer (that is, an oligonucleotide suitable for serving as a hybridization probe and/or as a primer for DNA or RNA synthesis along a complementary template) which includes a substantially purified single stranded oligonucleotide (an RNA or DNA molecule at least two nucleotides in length) containing a region the sequence of which is identical to the sequence of a six nucleotide, single stranded segment of a gene encoding a mutant form of a human photoreceptor protein, which segment includes part or all of the mutation. If the probe/primer is intended to serve as a primer, the mutation is preferably located at the 3' end of the segment. The term "photoreceptor protein" means any protein which is expressed solely or predominantly by retinal cells, including cells of the retinal pigment epithelium; preferably it is one of the following: a cone visual pigment, a subunit of rod transducin, a subunit of cone transducin, a subunit of retinal cGMP phosphodiesterase, interphotoreceptor retinal binding protein, or, more preferably, rhodopsin. Where the photoreceptor protein is rhodopsin, the mutation preferably includes a change in the codon encoding proline 23 (see FIG. 1), such as a substitution of a histidine codon for the proline 23 codon by, for example, a C to A transversion in the second nucleotide of that codon.

The probe/primer of the invention may be used in either of two methods, each of which is useful for detecting a mutation in a gene encoding a human photoreceptor protein, or for diagnosing an HRD disease (preferably RP) in a human fetus or patient, or for detecting, in a human fetus or patient, a genetic predisposition to develop such a disease. One of the two methods includes the following steps:

(a) providing the probe/primer of the invention, (b) exposing the probe/primer to a nucleic acid sample obtained or derived from the individual to be tested, and (c) detecting hybridization of the probe/primer to the nucleic acid sample. The nucleic acid sample may be RNA, cDNA, genomic DNA, or DNA amplified by cloning or PCR.

The other such method involves the following steps:

(a) providing the probe/primer of the invention;

(b) combining this probe/primer with a second primer and a nucleic acid sample (generally but not necessarily genomic DNA) derived from the individual to be tested, under conditions permitting a detectable difference in the extent of amplification (i.e., the making of multiple DNA copies) of a nucleic acid template which includes the mutant sequence, compared to the extent of amplification of the corresponding section of a normal allele; and (c) detecting (e.g., by ethidium bromide staining of a gel) the extent of amplification which took place. The second primer is an oligonucleotide that includes a sequence identical to that of a six-nucleotide segment of the template DNA, which segment is located (i) on the DNA strand complementary to the strand on which the probe/primer segment of the gene is located, and (ii) on the opposite side of the mutation from the probe/primer segment of the gene, such that the probe/primer and the second primer together are suitable for priming the amplification, by multiple cycles of polymerase chain reaction ("PCR"), of a section of template DNA that encompasses the mutation.

The invention also provides for a method of preparing such a probe/primer, which method includes the steps of (a) providing a sample of nucleic acid (i.e., genomic DNA, cDNA, or mRNA) obtained or derived from a patient with an HRD disease (preferably RP);

(b) amplifying a portion of the nucleic acid, which portion includes a fragment of a gene encoding a mutant form of a human photoreceptor protein, which fragment includes part or all of the mutation (i.e., part or all of the segment of the mutant gene sequence which differs from the sequence of the normal allele is included in the sequence of the fragment);

(c) sequencing (i.e., determining the DNA sequence of) the amplified nucleic acid; and (d) preparing a single stranded oligonucleotide (preferably DNA) containing a region the sequence of which is identical to the sequence of a six-nucleotide segment of the amplified nucleic acid, which segment includes part or all of the mutation.

In another aspect, the invention features a transgenic non-human mammal (preferably a mouse), some or all of whose nucleated cells contain a gene encoding a mutant form of a human photoreceptor protein, which gene was introduced into the mammal, or an ancestor of that mammal, at an embryonic or germ cell stage. This "embryonic stage" may be any point from the moment of conception (e.g., as where the sperm or egg bears the foreign gene) throughout all of the stages of embryonic development of the fetus. A "transgenic mammal" herein denotes a mammal bearing in some or all of its nucleated cells one or more genes derived from a different species; if the cells bearing the foreign gene include cells of the animal's germline, the gene may be transmissable to the animal's offspring. The photoreceptor protein is preferably selected from the group consisting of rhodopsin, a cone visual pigment, a subunit of rod transducin, a subunit of cone transducin, a subunit of retinal cGMP phosphodiesterase, and interphotoreceptor retinal binding protein. More preferably, the photoreceptor protein is rhodopsin and the gene encoding it has, most preferably, a mutation in the codon normally encoding rhodopsin proline 23.

The probe/primers of the invention provide a simple and highly accurate means of diagnosing certain HRD diseases, including those involving defects in the genes encoding rhodopsin and other photoreceptor proteins. The diagnostic assay can be carried out on DNA from virtually any nucleated cells of the patient, including easily obtained cells such as leukocytes. Once a particular genetic defect has been identified in a given HRD disease patient, family members of that patient may be conveniently tested for the presence of that genetic defect and thus for their expected susceptibility to the same disease and their status as carriers of the defect. In particular, by applying the assay of the invention to cells obtained by amniocentesis, a fetus can be tested while still in utero. Treatment to forestall the progress of the disease could thus be begun prior to the onset of any physical symptoms.

The invention also provides a means of creating animal models for HRD diseases, which, chiefly because the affected tissue is solely located within the eye, have proven very difficult to study in humans. The transgenic animals will provide a way to develop and test potential therapies for the various HRD diseases, and may eventually lead to cures for these devastating illnesses.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1a–1e is the nucleotide sequence of the gene encoding normal human rhodopsin, with the corresponding amino acid sequence shown below the nucleotide sequence and with the placement but not the full sequence of each of the five rhodopsin introns indicated; codon 23 is circled (adapted from FIG. 2 of Nathan and Hogness, Proc. Natl. Acad. Sci. USA 81:4851–4855, 1984).

FIG. 2a–2g the nucleotide sequence of the entire gene encoding normal human rhodopsin, including the full sequence of each intron, with numbered boxes drawn around the sequences which correspond to PCR primers utilized to amplify the various exons (sequence obtained from Genbank Accession No. K02281, EMBL ID:HSOPS).

FIG. 3 is a DNA sequencing gel analysis of codons 20 to 26 of rhodopsin genes obtained from three patients with autosomal dominant RP.

FIG. 4 is an illustration of the nucleotide sequences of (a) a 19mer oligonucleotide probe with a C-to-A transversion mutation in codon 23 (underlined), (b) the corresponding 19mer oligonucleotide probe with the normal proline 23 codon, (c) a 15mer oligonucleotide probe with the C to-A transversion mutation in codon 23, and (d) the corresponding 15mer oligonucleotide probe with the normal proline-23 codon.

Figure 7:
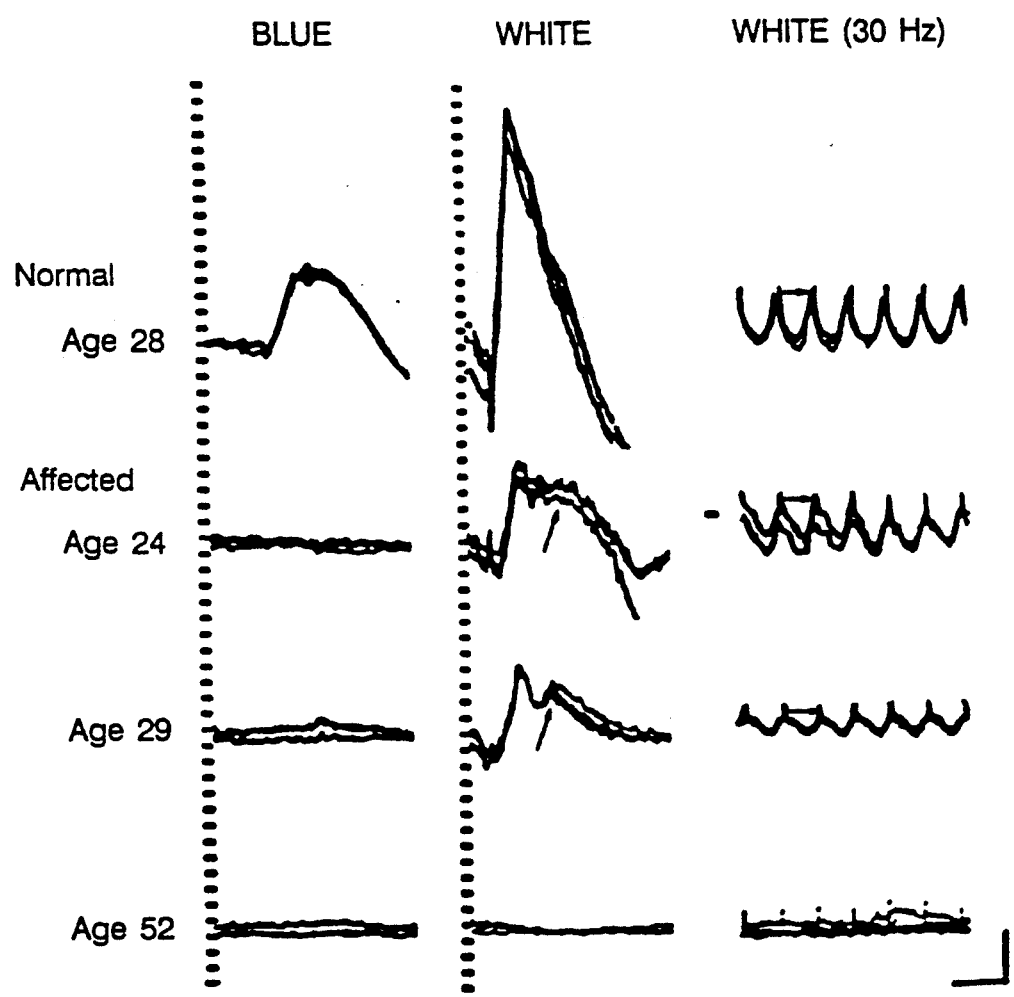

FIG. 7 is a comparison of full-field ERGs from an unaffected individual (age 28), her two affected siblings (ages 24 and 29), and an affected aunt (age 52) in family #5850 with autosomal dominant RP.

FIG. 8 is the sequence of a portion of the human rhodopsin gene from nucleotide #211 to #390, showing the sequences (boxed) of PCR primers #348, 485, and #502, wherein #485 and #502 are identical except for their 3' nucleotides.

Figure 9:
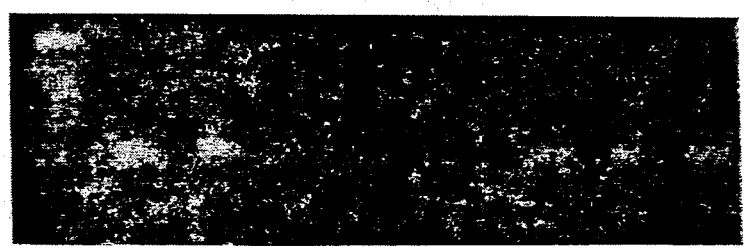

FIG. 9 is a photograph of an agarose gel in which the products of PCR amplification of the DNA of a patient with a C to A mutation in codon 23 of one rhodopsin allele (lanes 2 and 7) and that of an individual with two normal rhodopsin alleles (lanes 3 and 8) are compared to that of a mutation bearing control (lanes 1 and 6).

FIG. 10 is the cDNA sequence of the γ-subunit of human retinal cGMP phosphodiesterase.

FIG. 11 is the DNA sequence of the longest open reading frame in the cDNA sequence of FIG. 10, with amino acid residues shown below corresponding codons.

DIAGNOSIS OF HRD DISEASES

The invention disclosed herein relates to diagnosis of various HRD diseases by first identifying the genetic defect which causes the disease in question, and then devising an assay using either a hybridization probe or a PCR amplification primer containing the mutant sequence. It is postulated that many, if not all, of such diseases are attributable to mutations in the various photoreceptor proteins, including but not limited to rhodopsin, the cone visual pigments, rod transducin, cone transducin, retinal cGMP phosphodiesterase, and interphotoreceptor retinal binding protein. As a test of this hypothesis, rhodopsin genes from several patients with autosomal dominant Rp were examined by the method of the invention for the presence of any deviation from the normal DNA sequence for such gene. Although some forms of inherited RP are believed to be associated with genetic defects in genes distinct from the rhodopsin gene (e.q., on chromosomes 1 and X), this examination of the rhodopsin genes of affected patients, described in detail in Example 1 below, showed that at least one type of RP involves a point mutation in one rhodopsin allele of affected patients.

After identifying a specific mutation that is associated with a particular HRD disease, that information can then be used to design an oligonucleotide useful as a diagnostic tool to screen other individuals for that particular disease. The oligonucleotide can take the form of a hybridization probe (described in Example 2) or a primer for PCR amplification (described in Example 3). Such hybridization probes could range in size from six to 10,000 nucleotides (preferably 13 to 20 nucleotides), while PCR primers could range from ten to 1000 nucleotides (preferably 18 to 25 nucleotides).

If either such screen reveals that the mutation appears in some patients with an autosomal dominant HRD disease but in no unaffected individuals of a statistically significant sample, it can be presumed that the existence of that mutation in the DNA of any tested individual will be informative for the inherited propensity to develop one form of autosomal dominant HRD disease, and an oligonucleotide which includes the mutant sequence will be useful as a diagnostic tool for screening individuals for that form of the disease. Alternatively, a mutation first identified in the DNA of an individual with autosomal recessive HRD disease would be expected to appear as a homozygous trait in related patients also exhibiting autosomal recessive HRD disease, and either not appear, or appear in only a single allele, in normal individuals. A genetic screening test utilizing an oligonucleotide including this mutation and a second oligonucleotide with the normal sequence could be useful not only to detect those homozygous for the mutation (and thus destined to develop the disease), but also those heterozygous for the mutation (and thus carriers of the disease trait).

A further application of the information gleaned by the method of the invention is illustrated in Example 4, wherein is described the creation of a transgenic animal bearing a gene for a mutant form of a human photoreceptor protein. This animal is designed to serve as an animal model for a particular HRD disease.

EXAMPLE 1

Figure 1A:
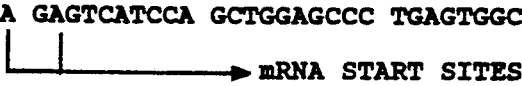

The nucleotide sequence for the normal human rhodopsin gene has been published (Nathans and Hogness, Proc. Natl. Acad. Sci. USA 81:4851–4855, 1984; also Genbank Accession No. K02281, EMBL ID:HSOPS), and is shown in FIGS. 1 (without introns) and 2 (with introns). Using this sequence information, four pairs of 20-base oligodeoxyribonucleotides having the sequences shown in FIG. 2 were synthesized using an automated DNA synthesizer (Pharmacia Gene Assembler), following manufacturer's instructions. The pair with the sequences numbered 348 and 349 in FIG. 2 were designed to prime the PCR amplification of exon 1 of the rhodopsin gene, 346 and 347 to prime exon 2, 344 and 345 to prime exons 3–4, while 350 and 351 were designed to prime the translated sequence within exon 5.

Figure 3:
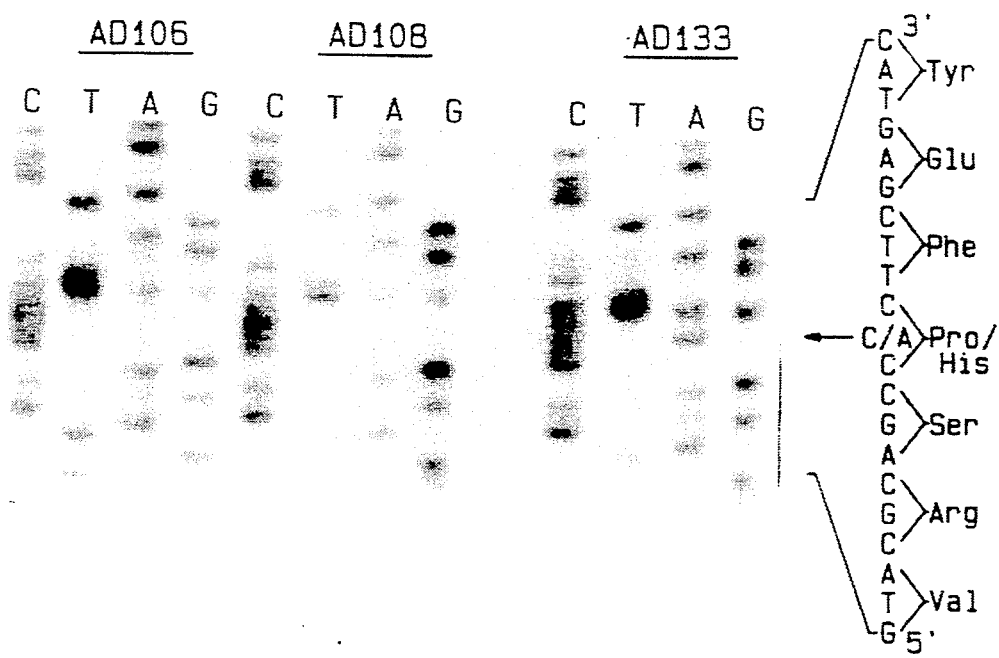

Twenty unrelated patients with autosomal dominant RP were selected from families whose affected members had delayed rod ERG responses and either normal or delayed cone ERG responses. A 0.05 to 0.5 μg sample of leukocyte DNA from each patient was amplified using 35 cycles in an automated PCR machine (Ericomp Programmable Cyclic Reactor) and one of the pairs of oligonucleotide primers listed above. This amplification process was repeated for each patient using each of the other pairs of oligonucleotide primers. Sequence analysis of the resultant amplified DNA using the method of Yandell and Dryja (Cold Spring Harbor Symposium Series: Cancer Cells 7-Molecular Diagnostics of Human Cancer; eds. Furth and Greaves, 223–227, Cold Spring Harbor Press, Cold Spring Harbor, N.Y., 1989) revealed that five of the 20 patients were heterozygous for the same C-to-A transversion within codon 23 (for example, see AD133 in FIG. 3).

EXAMPLE 2

Using the rhodopsin mutation sequence information described in Example 1, two 19-nucleotide oligonucleotide hybridization probes [shown in FIG. 4(a) and (b)] and two having 15 nucleotides each [FIG. 4(c) and (d)] were then synthesized. The sequences of two of these oligonucleotides [FIG. 4(a) and (c)] match the sequences of codon-23-containing segments of the mutant rhodopsin gene, while the sequences of the other two probes [FIG. 4(b) and (d)] match the sequences of the corresponding segments of the normal rhodopsin gene. The 19mer probes illustrated in FIG. 4(a) and (b) constitute the pair of probes utilized for some of the hybridization tests described herein; the 15mer pair of probes illustrated in FIG. 4(c) and (d) were found to hybridize with the same specificity as the longer probes, and so were substituted for the longer probes in some of the work described herein. Hybridization and washing conditions were identical in all cases, except as specified below.

DNA from each of 148 unrelated patients with autosomal dominant RP, as well as DNA from each of 102 normal individuals who were unrelated to the patients, was screened using one of the pairs of oligonucleotide probes in a hybridization assay, as follows: Leukocyte DNA from each subject was amplified by PCR, using as amplification primers the pair of oligonucleotides flanking exon 1 (primers #348 and #349). The resultant amplified DNA, which included the exon 1 sequences of each subject's two rhodopsin gene homologous, was purified by electrophoresis in a 2% agarose gel (Seakem), denatured in situ by incubating for 2% min in 0.5M NaCl and 0.5M NaOH, and transferred by Southern blotting techniques to a nylon membrane filter (Micron Separations, Inc.) for hybridization analysis. The membranes were baked at 80° C. for 2 hours, then prehybridized overnight at 37° C. in 30–50 ml of a solution containing 0.5% SDS, 100 mM sodium pryophosphate, 5X SSPE (1 liter of 20X SSPE contains: 174 g NaCl, 27.6 g NaH$_2$PO$_4$(H$_2$O), 7.4 g disodium EDTA, pH 7.4), and 5X Denhardts (500 ml of 50X Denhardts contains: 5 g Ficol (M.W. 400,000), 5 g polyvinylpyrolidone, and 5 g bovine serum albumin). Each oligonucleotide probe, end labeled with $^{32}$P using [γ-$^{32}$P]-dATP and polynucleotide kinase (New England Biolabs), was tested for its ability to hybridize with the denatured amplified DNA under highly-stringent conditions, as follows: the pre hybridization solution was replaced with 5–10 ml of fresh solution containing the labelled oligonucleotide probe; after hybridization for 1–2 hours at 37° C. the filters were washed 4 times at room temperature in a solution of 0.5X SSC and 0.1% SDS; and then washed for 20 minutes at 57° C. (for the 9mer probes) or 53° C. (for the 15mer probes) in a solution of 3M tetramethylammonium chloride, 50mM Tris (pH 8.0), 2 mM EDTA, and 0.1% SDS. The filters were then rinsed at room temperature with fresh aliquots of the same wash solution, blotted on Whatman 3M paper, wrapped in clear plastic wrap (Saran Wrap), and autoradiographed, with exposures generally for 2–40 hours at −70° C., using an intensifyinq screen. As the washing procedure utilized removes unhybridized labeled probe from the filter but leaves in place on the filter any probe which has hybridized to the amplified rhodopsin DNA, autoradiographic analysis of the filter detects only hybridized probe. Hybridization of the mutation-containing probe [FIG. 4(a) or (c)] with a given sample of DNA indicates the presence of that mutation in the genome of the person from whom the sample was derived. Of the 148 RP patients tested, 17, including the original five who had previously been identified by sequence analysis as bearing the mutation, carried the C-to-A base change in codon 23, whereas none of the 102 normal individuals tested carried it ($X^2 = 12.57$, $p < .001$). This result effectively rules out the possibility that this nucleotide change represents a DNA polymorphism with no relationship to RP.

Figure 5:
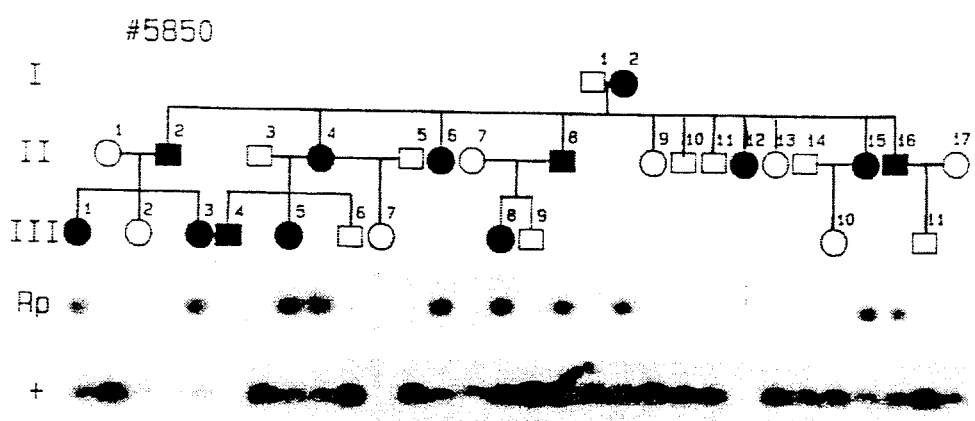
FIG. 5 is an illustration of the inheritance of RP within one family (designated pedigree #5850), showing the hybridization of amplified rhodopsin gene exon 1 DNA obtained from each indicated individual with (1) an oligonucleotide probe bearing the mutant sequence within codon 23 (line marked "RP") or (2) an oligonucleotide with the normal sequence (line marked "+").

The potential utility of these probes to screen for inheritance of this form of RP is illustrated by a study of inheritance within a single family, family #5850. As shown in the autoradiograms across the bottom of FIG. 5, the C-to-A mutation ("Rp") is present in amplified leukocyte DNA from all affected members (solid symbols) who were tested, but in none of the amplified DNA samples from unaffected members (open symbols) who were tested. Leukocyte DNA for testing was unavailable from individuals II- 2, II-12, III- 4, and III- 7.

Figure 6:
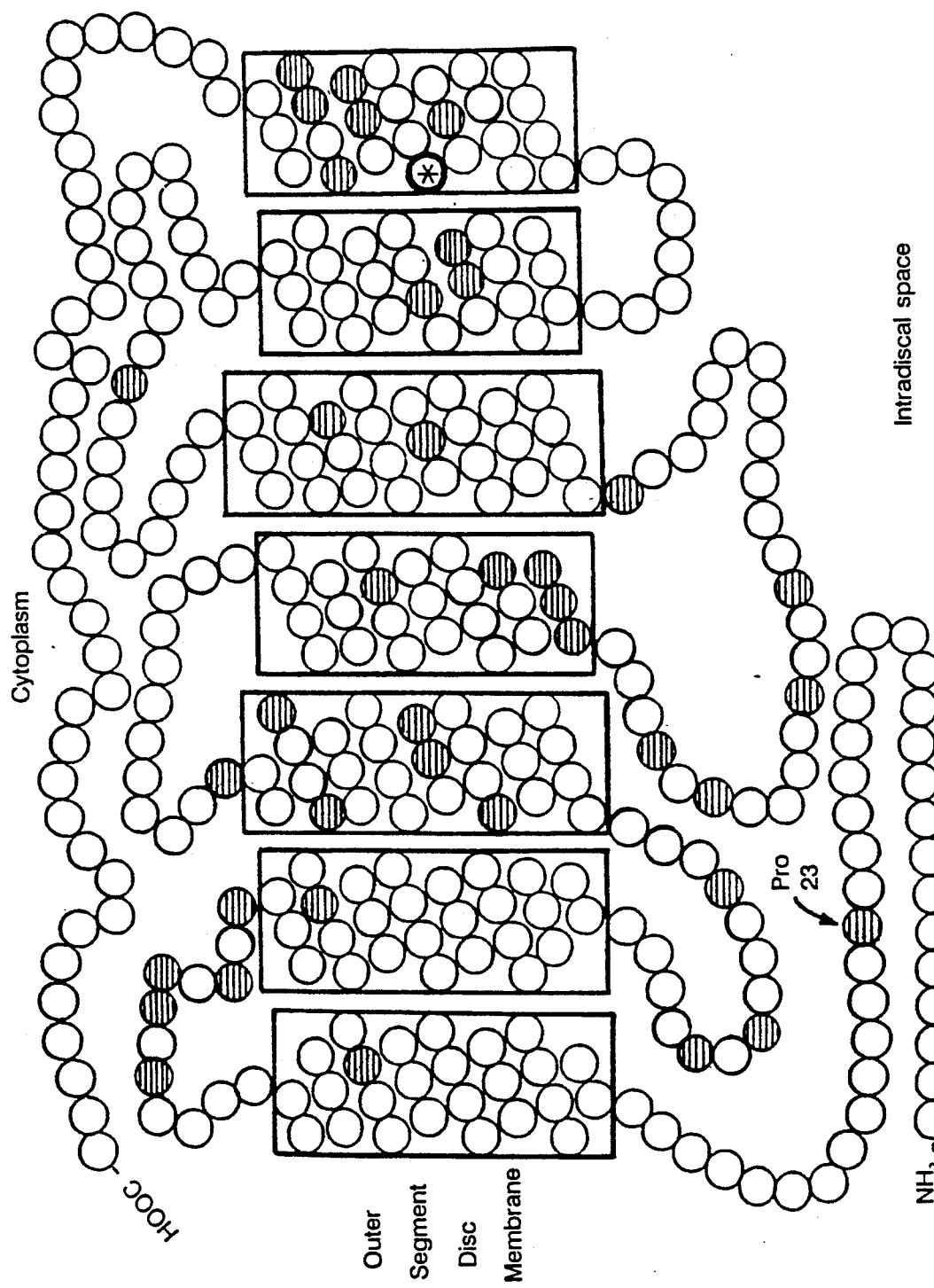
FIG. 6 is a schematic representation of the approximate arrangement of the rhodopsin molecule, in which codon 23 codes for proline in the normal molecule, in relation to the rod outer segment disc membrane.

Codon 23 normally codes for a proline within the amino terminal region of rhodopsin (FIG. 6). The precise function of this region of the protein is unknown, but the proline at this position is invariate among the vertebrate and invertebrate opsins, as well as among molecules such as the beta 2 adrenergic receptor that have homology with the opsins. In view of the conservation of proline at this position, the nucleotide change found in codon 23 (i.e., the substitution of the charged amino acid histidine for the nonpolar proline) was predicted to result in a dysfunctional or absent rhodopsin molecule that would affect rod function.

This prediction is consistent with ERG findings in family #5850. FIG. 7 illustrates normal ERG responses from an unaffected member (III-2, age 28) and abnormal responses from two affected siblings and an affected aunt (III- 3, age 24; III-1, age 29; and II-4, age 52). The techniques used to obtain the ERG data are as described by Berson et al. (Arch. Ophthalmol. 80: 58–67, 1968) and Reichel et al. (Am. J. Ophthalmol. 108: 540–547, 1989). Stimulus onset is indicated in the left and middle columns of FIG. 7 by vertical hatched lines, and in the right column by a vertical line. Two or three consecutive sweeps are superimposed. Cornea positivity is indicated by upward deflection. Oblique arrows in the middle column designate delayed rod dominated peaks. Horizontal arrows in the right column designate cone response times (i.e., time interval between stimulus flash and corresponding cornea-positive response peak). Under these test conditions, normal amplitudes are $\geq 100$ $\mu V$ for single flashes of blue light, $\geq 350$ $\mu V$ for single flashes of white light, and $\geq 50$ $\mu V$ for 30 Hz white flicker; normal cone response times are $\geq 32$ msec. The calibration symbol in the lower right corner of FIG. 7 designates 50 msec horizontally and 100 $\mu V$ vertically.

The recordings in the left column of FIG. 7 show the response to flashes of dim blue light, a measure of rod function. The two affected siblings have a markedly reduced response of the rods compared to the response shown by their unaffected sister. The middle column of FIG. 7 shows the response to single flashes of white light, which normally elicit a response from both rods and cones. The cone dominated and the rod-dominated ERG peaks recorded by the 28-year old normal member occurred at the same time and cannot be distinguished, while her two affected siblings exhibit a splitting of the response into an early, cone-dominated peak and a delayed, rod dominated peak of reduced amplitude (see oblique arrows in FIG. 7). This splitting results from a relatively normal cone response time but delayed rod response time. The right column of FIG. 7 shows the ERG responses of the four family members to flickering (30 Hz) white light; this is a measure of cone function, since only cones can respond to light flashes of this frequency. In this test, the 24-year-old affected sibling demonstrates a normal amplitude and response time similar to that of her unaffected sister, while the 29-year-old affected sibling, with more advanced disease, has a slightly reduced amplitude and borderline delayed response time (see horizontal arrows). The ERG findings in the two affected siblings are consistent with the predominant involvement of rods in the early stages of this form of autosomal dominant RP, as one might expect from a defect in rhodopsin, a protein that is thought to be associated exclusively with rods. Late in this disease, there is loss of cone and rod function, illustrated by the profoundly reduced responses in all three columns from the 52-year-old affected aunt.

EXAMPLE 3

Instead of using radioactively labelled hybridization probes to screen genomic DNA for the mutation in codon 23, as described in Example 2, the inherent disadvantages of radioactive reagents may be avoided entirely by screening instead with a method which uses PCR primer discrimination to indicate the presence of a mutant allele. This method was used to screen samples of genomic DNA for the C to A transversion in codon 23 of rhodopsin, as follows:

Two pairs of 20-base oligonucleotide primers were synthesized and used to prime PCR amplification of a 151 bp segment of rhodopsin DNA from each patient to be screened. One of the pairs is shown in FIG. 8 as the boxed sequences numbered 348 and 502, with oligonucleotide #502 including as its 3′ nucleotide the (G) corresponding to the normal sequence found in the antisense strand of codon 23. The second pair of primers is shown in FIG. 8 as the boxed sequences numbered 348 and 485, with oligonucleotide #485 identical to #502 except that its 3′ nucleotide is (T), corresponding to the mutant sequence for the antisense strand of codon 23. A perfect match of primer to template at the 3′0 nucleotide of each PCR primer is known to be particularly important for efficient amplification of the intervening template DNA. Thus, the 348/485 pair of primers will be capable of efficiently priming amplification only of DNA containing the mutant allele, while the 348/502 pair will efficiently prime amplification only of DNA which has the normal sequence in codon 23, i.e. the normal allele. Efficiency of priming is measured as follows:

A 50 ng sample of leukocyte genomic DNA from an individual to be screened is combined with 20 picomoles of primer #348 and 20 picomoles of primer #485 in a total volume of 50 μl PCR reaction solution (50 mM KCl, 20 mM Tris pH 8.4, 0.1 μg/μl bovine serum albumin, 1.0 mM MgCl$_2$, and 200 μM of each of dATP, dCTP, dGTP and dTTP). A second 50 ng sample of genomic DNA from the same individual is similarly combined with 20 picomoles of primer #348 and 20 picomoles of primer #502 in 50 μl PCR solution; both samples are overlaid with 50 μl sterile mineral oil and simultaneously subjected to the same thermal cyclic reactor block in an automated PCR machine (Ericomp Programmable Cyclic Reactor) under the following temperature conditions: 93° C. for 2 min; 35 repetitions of the cycle: 46° C. for 10 sec, 71° C. for 30 sec, and 93° C. for 20 sec; and finally, one cycle of 46° C. for 90 sec, 71° C. for 4 min. Mineral oil is removed by extracting with 55 μl of a solution of 96% chloroform and 4% isoamyl alcohol. Seven μl of the amplified product is electrophoresed through a 2% agarose gel with appropriate size markers, stained with ethidium bromide, and either photographed or observed directly under ultraviolet illumination. Only DNA which has been efficiently amplified will form a clearly stained band on the gel. Thus, only those individuals who carry the mutant allele will show a visibly stained band in the lane corresponding to the 348/485 primer pair. Both normal individuals and those heterzygous for the mutant allele will produce a distinct band of amplified DNA in the 348/502 lane. As a control, two samples (one for each pair of primers) from an individual known to carry the mutant allele are always amplified alongside the test sample. In FIG. 9, DNA from three patients, two (lanes 1 and 6, and lanes 2 and 7, respectively) having both a normal and a mutant allele, and a third (lanes 3 and 8) having two normal alleles, was amplified by PCR using either the 348/485 primer pair (lanes 1, 2, and 3) or the 348/502 primer pair (lanes 6, 7, and 8); the patients bearing the mutant allele showed efficient priming with either primer pair, while the homozyqous normal individual produced a distinct band only when 348/502 primer pair was used (lane 8) and not when the 348/485 primer pair was used (lane 3).

EXAMPLE 4

In order to create an animal model for human RP, the gene encoding the mutant form of human rhodopsin characterized above was first isolated by screening a genomic DNA library prepared from a sample of DNA obtained from an RP patient who had been shown by the method of the invention to carry the C-to-A transversion in one allele. The probe used to screen the library was a 6 kilobase DNA fragment that encodes the entire normal rhodopsin gene, including its transcriptional and translational control elements. Given the length of the probe, it would be expected to hybridize equally well with the mutation containing rhodopsin allele and the normal allele, so of the clones from this library which hybridize to the probe, one half are expected to represent the mutant gene. Positive clones can then be further screened to identify the mutant allele by using either the probes of Example 2 or the PCR primers of Example 3. Once the mutant rhodopsin gene is isolated, it will be introduced into a mouse embryo in accordance with the method of Leder et al. U.S. Pat. No. 4,736,866 (herein incorporated by reference). The strain of transgenic mice which results will bear one gene for mutant human rhodopsin and two for normal mouse rhodopsin; crossing two such mice will yield some offspring which bear two mutant human alleles and two normal mouse alleles, the 1:1 proportion which in humans results in autosomal dominant RP. It is expected that such a genotype will result in expression of a phenotype resembling human RP, thus providing an invaluable means to study in detail the nature of the disease, and to test potential therapies.

OTHER EMBODIMENTS

Other embodiments are within the following claims. For example, the method disclosed herein for identifying the precise genetic abnormality responsible for a given HRD disease could be utilized for further studies on the rhodopsin gene, with the goal of identifying mutations other than the one described in Example 1 above. Such mutations might include, besides point mutations similar to the C-to A transversion described above, deletions, additions, or rearrangements of one or more nucleotides. Alternatively, the method could be applied to genes encoding other photoreceptor proteins besides rhodopsin, or for other eye-related proteins with a possible role in HRD disease. For example, genes encoding the following human photoreceptor proteins have been cloned and sequenced and thus could be analyzed by the method of the invention to determine whether or not a mutation in any such gene is associated with some form of the disease: each of the three cone visual pigments (Nathans et al., Science 232:193, 1986); interphotoreceptor retinal binding protein (Fong and Bridges, J. Biol. Chem. 263: 15330, 1988); retinal S antigen (Yamaki et al., FEBS Lett. 234: 39, 1988); the α-subunits of rod transducin and cone transducin (Lerea et al., Science 234:77, 1986); and the Y-subunit of retinal cGMP phosphodiesterase (for which the cDNA sequence and the corresponding amino acid sequence of the longest open reading frame are shown in FIG. 10 and FIG. 11, respectively; this DNA sequence was determined by sequencing a cDNA clone obtained by probing a human retina cDNA library with a synthetic oligonucleotide probe, the sequence of which was derived from a conserved region found to be identical in two previously cloned homologs of the gene, the bovine and the murine versions). Genetic linkage studies will in some cases suggest likely gene candidates for analysis by the method of the invention, as where the inherited trait maps to the same chromosomal location as a particular cloned and sequenced gene. If such map information is not available for a given gene or HRD disease, then a bank of appropriate PCR primers representing all suspected genes can be used by applying the methods of the invention in a brute force search for the causative mutation. Where the DNA sequence of a given photoreceptor protein-encoding gene is not known, it can be determined by standard cloning and DNA sequencing techniques well known to those of ordinary skill in the art (see, e.q., Maniatis et al., Molecular Cloning: A Laboratory Manual. Cold Spring Harbor Laboratory, Cold Spring Harbor, N.Y., 1982).

Once the mutation responsible for a given HRD disease has been characterized, an oligonucleotide probe/primer incorporating the mutation can be readily synthesized by standard methods; the probe/primer could then be used to screen nucleic acid samples in the same manner as the probe disclosed in Example 2 or the primer described in Example 3. A second probe/primer having the sequence of the corresponding part of the normal version of the gene may also be synthesized for use as a control capable of hybridizing to, or priming the amplification of, the normal allele. The probe/primers could be longer or shorter than the 19mers and 15mers utilized in Example 2 or the 20mers of Example 3, as long as they can clearly differentiate between the mutant allele and the normal allele.

Minor variations in the methods used would also be within the scope of the invention. For example, if a source of mRNA encoding the protein of interest were available from HRD disease patients, cDNA cloning could substitute for PCR as the method used for amplifying the number of copies of mutation-containing DNA in a given DNA sample, in order to generate enough copies for DNA sequence analysis. The probe/primer of the invention may be RNA rather than DNA (although DNA, which is less labile than RNA, would be preferred), and the nucleic acid to be screened using the probe/primer could be mRNA or cDNA (if either is available) instead of genomic DNA. Any suitable animal could be substituted for the mouse of Example 4 in order to produce an animal model for an HRD disease; the method of introducing the heritable human mutant allele into the animal may vary from that specified herein, and still be within the invention: for example, the mutant human gene may be introduced solely into those cells of a developing embryo which are already committed to develop into eye cells, yielding an animal which bears the mutant allele in its eye cells (e.g., retinal cells) but not in the majority of its other cells. The particular form of HRD disease to be investigated may be one that is inherited in an autosomal dominant manner, as is the form of RP discussed in the above Examples, or it could be autosomal recessive, X linked, or mitochondrially (maternally) inherited. Hybridization of the probe/primer to the nucleic acid sample, or efficient amplification of a sample by the probe/primer, could be detected by any appropriate means known to those of ordinary skill in the art.

What is claimed is:

1. A probe or primer consisting essentially of a substantially purified single-stranded oligonucleotide, said oligonucleotide being of 13–25 nucleotides in length and containing a region the sequence of which is identical to a six-nucleotide segment of a gene encoding a mutant form of rhodopsin, said segment comprising part or all of a mutation characterizing said mutant form.

2. The probe or primer of claim 1, wherein said oligonucleotide is DNA.

3. The probe or primer of claim 1, wherein said mutation comprises a change in the codon encoding rhodopsin proline 23.

4. The probe or primer of claim 3, wherein said change is the substitution of a histidine codon for said proline 23 codon.

5. The probe or primer of claim 4, wherein said change is a C-to-A transversion in the second nucleotide of said codon.

6. The probe or primer of claim 1, wherein said mutation is located at the 3' end of said segment.

* * * * *

UNITED STATES PATENT AND TRADEMARK OFFICE
CERTIFICATE OF CORRECTION

PATENT NO. : 5,225,546
DATED      : July 6, 1993
INVENTOR(S): Thaddeus P. Dryja and Eliot L. Berson It is certified that error appears in the above-indentified patent and that said Letters Patent is hereby corrected as shown below:

Column 6, line 51, correct "homologous" to --homologues--;

Column 6, line 53, correct "2% min" to --20 min--;

Column 7, line 6, correct "9mer probes)" to --19mer probes)--.

Signed and Sealed this

Twenty-ninth Day of March, 1994

*Attest:*

BRUCE LEHMAN

*Attesting Officer*    Commissioner of Patents and Trademarks

UNITED STATES PATENT AND TRADEMARK OFFICE
CERTIFICATE OF CORRECTION

PATENT NO.    : 5,225,546

DATED         : July 6, 1993

INVENTOR(S)   : Thaddeus P. Dryja and Eliot L. Berson

It is certified that error appears in the above-identified patent and that said Letters Patent is hereby corrected as shown below:

Column 1, line 4 or 5, add the following:

--This invention was made with government support under Grant No. EY02014 awarded by the National Institutes of Health. The government has certain rights in the invention.--

Signed and Sealed this

Twentieth Day of June, 1995

Attest:

BRUCE LEHMAN

*Attesting Officer*    *Commissioner of Patents and Trademarks*